(12) United States Patent
Franc et al.

(10) Patent No.: US 7,655,697 B2
(45) Date of Patent: Feb. 2, 2010

(54) ORAL PHARMACEUTICAL COMPOSITION FOR TARGETED TRANSPORT OF A PLATINUM COMPLEX INTO THE COLORECTAL REGION, METHOD FOR PRODUCING AND USE AS MEDICAMENT THEREOF

(75) Inventors: Ales Franc, Brno (CZ); Petr Sova, Hradec Králové (CZ)

(73) Assignee: Pliva-Lachema A.S., Brno (CZ)

( * ) Notice: Subject to any disclaimer, the term of this patent is extended or adjusted under 35 U.S.C. 154(b) by 0 days.

(21) Appl. No.: 11/574,929

(22) PCT Filed: Sep. 14, 2005

(86) PCT No.: PCT/CZ2005/000070

§ 371 (c)(1),
(2), (4) Date: Mar. 8, 2007

(87) PCT Pub. No.: WO2006/029579

PCT Pub. Date: Mar. 23, 2006

(65) Prior Publication Data
US 2007/0232819 A1    Oct. 4, 2007

(30) Foreign Application Priority Data
Sep. 14, 2004    (CZ) .................................. 2004-964

(51) Int. Cl.
*A61K 31/28* (2006.01)
(52) U.S. Cl. ........................................ 514/492
(58) Field of Classification Search ............... 514/492
See application file for complete search history.

(56) References Cited

U.S. PATENT DOCUMENTS

| | | | | |
|---|---|---|---|---|
| 3,920,819 A * | 11/1975 | Stephens et al. | ............ | 514/209 |
| 4,079,128 A * | 3/1978 | Lin et al. | ....................... | 514/23 |
| 4,696,918 A * | 9/1987 | Stoddart et al. | ............... | 514/58 |
| 4,845,124 A * | 7/1989 | Kidani et al. | ................ | 514/492 |
| 5,072,011 A * | 12/1991 | Abrams et al. | ............... | 556/137 |
| 5,194,645 A * | 3/1993 | Barnard | ....................... | 556/137 |
| 5,196,555 A * | 3/1993 | Kaplan et al. | ................ | 556/137 |
| 5,244,919 A * | 9/1993 | Abrams et al. | ............... | 514/492 |
| 5,393,909 A * | 2/1995 | Khokhar et al. | .............. | 556/137 |
| 5,409,915 A * | 4/1995 | Farrell et al. | ................ | 514/187 |
| 5,434,256 A * | 7/1995 | Khokhar et al. | .............. | 556/137 |
| 5,603,777 A * | 2/1997 | Ohashi | ....................... | 134/25.4 |
| 5,998,648 A * | 12/1999 | Sohn et al. | ................. | 556/137 |
| 6,008,395 A * | 12/1999 | Kidani | ......................... | 556/137 |
| 6,025,473 A * | 2/2000 | Deeley et al. | ................ | 530/350 |
| 6,136,336 A * | 10/2000 | Tanaka et al. | ................ | 424/434 |
| 6,340,770 B1 * | 1/2002 | Kwon et al. | ................. | 556/137 |
| 6,350,737 B1 * | 2/2002 | Zak et al. | ........................ | 514/58 |
| 6,413,953 B1 * | 7/2002 | Gianomenico et al. | ...... | 514/188 |
| 6,503,943 B1 * | 1/2003 | Zak et al. | ..................... | 514/492 |
| 6,518,428 B1 * | 2/2003 | Wong et al. | ...................... | 546/2 |
| 6,544,962 B1 * | 4/2003 | Jones et al. | .................... | 514/49 |
| 6,630,124 B1 * | 10/2003 | Gozes et al. | ................ | 424/1.69 |
| 6,894,049 B1 * | 5/2005 | Wong et al. | ............... | 514/252.1 |
| 7,108,845 B2 * | 9/2006 | Smith | ......................... | 424/9.1 |
| 7,135,191 B2 * | 11/2006 | Hertelendy et al. | .......... | 424/433 |
| 2003/0109487 A1 * | 6/2003 | Jones et al. | .................... | 514/49 |
| 2004/0096499 A1 * | 5/2004 | Vaya et al. | ................... | 424/468 |
| 2004/0156888 A1 * | 8/2004 | Jensen et al. | ................. | 424/450 |
| 2006/0058311 A1 * | 3/2006 | Munzert et al. | .............. | 514/251 |
| 2006/0063832 A1 * | 3/2006 | Franc et al. | .................. | 514/492 |
| 2006/0099146 A1 * | 5/2006 | Chow et al. | ................... | 424/9.6 |
| 2006/0205810 A1 * | 9/2006 | Zong et al. | .................... | 514/492 |
| 2006/0246124 A1 * | 11/2006 | Pilkiewicz et al. | ........... | 424/450 |
| 2007/0048363 A1 * | 3/2007 | Salama | ........................ | 424/451 |

(Continued)

FOREIGN PATENT DOCUMENTS

CZ          200401167 A  *  3/2006

(Continued)

OTHER PUBLICATIONS

McKeage et al., Cancer Chemother Pharmacol, vol. 36, pp. 451-458 (1995).*

*Primary Examiner*—Porfirio Nazario Gonzalez
(74) *Attorney, Agent, or Firm*—Notaro & Michalos P.C.

(57) ABSTRACT

An oral pharmaceutical composition for targeted transport of a platinum complex into the colorectal region, includes a mixture of platinum complex of general formula I

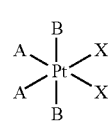

(I)

wherein A each independently is an —$NH_3$ group or an amino group containing 1 to 18 carbon atoms, B each independently is a halogen atom, a hydroxy group or a —O—C(O)—R group wherein R each independently is hydrogen atom or an alkyl, alkenyl, aryl, aralkyl, alkylamino or alkoxy group containing 1 to 10 carbon atoms or functional derivatives of these groups, and X each independently is a halogen atom or a monocarboxylate group containing 1 to 20 carbon atoms, or X together form a dicarboxylate group containing 2 to 20 carbon atoms, and at least one excipient selected from the group including a saccharide, oligosaccharide, polysaccharide, modified polysaccharide mucopolysaccharide, protein, oligoprotein, polyprotein, mucoprotein, peptide, oligopeptide and polypeptide, and optionally a lubricant and/or disintegrant, which mixture is optionally compressed into a tablet or contained in a capsule, and this tablet or capsule is optionally coated with a biodegradable layer and/or an outer pH-sensitive colonic layer, and a method of manufacturing and using the composition for treatment of colorectal carcinoma.

15 Claims, No Drawings

U.S. PATENT DOCUMENTS

2007/0128201 A1* 6/2007 D'Incalci et al. ......... 424/155.1
2007/0148249 A1* 6/2007 Franc .......................... 424/489
2007/0232819 A1* 10/2007 Franc et al. ................... 556/56
2007/0286905 A1* 12/2007 Salama ....................... 424/649
2008/0008740 A1* 1/2008 Franc et al. ................. 424/430

FOREIGN PATENT DOCUMENTS

WO  WO 2005077357 A1 *  8/2005
WO  WO 2005077385 A2 *  8/2005
WO  WO 2007147371 A 2    * 12/2007

* cited by examiner

ORAL PHARMACEUTICAL COMPOSITION FOR TARGETED TRANSPORT OF A PLATINUM COMPLEX INTO THE COLORECTAL REGION, METHOD FOR PRODUCING AND USE AS MEDICAMENT THEREOF

FIELD OF THE INVENTION

The invention relates to an oral pharmaceutical composition for a targeted transport of a platinum complex into the colorectal region, method for producing and use as medicament thereof.

BACKGROUND OF THE INVENTION

Colorectal carcinoma is a malignant tumor of the colon, in Europe belonging to the most widespread types of tumor diseases. Annually, almost 7 500 new cases of this disease are diagnosed and each year more than 4 000 of patients die of this disease. Over 50% of these tumors are localized in the rectum and 20% of them attack sigmoideum. Only about 15% of tumors were found in the colon proper, of them about 6 to 8% in the colon transversum and about 6 to 7% in the colon descendens. Despite differences in their anatomic location, the mentioned tumors are regarded as affection of one organ and are denoted as the colorectal carcinoma. Women suffer from colorectal carcinoma more often in the region of colon whereas men are more often affected in the rectal region. Clinical symptoms of colorectal carcinoma are manifested by its localization, magnitude of the mechanical obstruction and the overall response of the organism. The enterostenosis manifests itself by meteorism, change in defecation habits, colical pain, and in some cases by sudden ileus. An exulceration of the tumor manifests itself by microscopic or macroscopic bleeding and subsequent anemia.

Treatment of many tumor diseases makes use of platinum complexes. So far, the therapeutic practice uses only complexes of bivalent platinum, such as cisplatinum, carboplatinum and oxaliplatinum. However, these bivalent platinum complexes are unstable in the gastrointestinal tract and/or they are poorly absorbable by the organism. These properties of bivalent platinum complexes make their use in an oral dosage form impossible. Recently, it has been found that some of the new prepared complexes of tetravalent platinum retain their antitumor activity even when administered orally. Such complexes have been described in patent documents EP 0 328 274, EP 0 423 707 and PCT/CZ99/00015 as new substances for oral application.

Another possible application of platinum complexes is the rectal administration in which the platinum complex avoids the aggressive medium of the gastrointestinal tract and after absorption by the rectal mucosa it passes via the portal system directly into the systemic blood circulation. The possibility of rectal application of a tetravalent platinum complex has been described in U.S. Pat. No. 6,033,683.

In comparison with other application methods, oral administration of platinum complexes represents the most comfortable way for the patient and therefore oral application of a solid dosage form of a platinum complex, enabling release of the platinum complex only in the region of colon appears as very prospective and promising. Such oral colonic application of drugs has its history in application of antirheumatics or in protection of mucous membranes of the gastrointestinal tract by administration of peptides and proteins. In the mentioned cases, drugs or protective substances are applied orally in the form of their conjugates with auxiliary substances, particularly in the form of azo conjugates, cyclodextrin conjugates, glycoside conjugates, glucuronate conjugates, dextran conjugates, polypeptide conjugates and conjugates with polymers, or in a form protected by degradable polymer coating, particularly by a pH-sensitive or biodegradable polymer coating, or in a form sealed in capsules of a biodegradable polymer, preferably sealed in hard capsules, or in the form of a system of anchored drug or protective substance, preferably in the form of a biodegradable polymer and hydrogel matrices, or in the form of a pH-sensitive polymer matrices. All these systems protect the orally applied drug or protective substance from the aggressive medium of the gastrointestinal tract before it enters the large intestine.

Complexes of tetravalent platinum in general exhibit very poor solubility in water, low bulk density, low tap density, and a very high electrostatic charge. These properties represent a significant problem in the preparation of an oral solid dosage form. Moreover, complexes of tetravalent platinum are chemically unstable in contact with metals or with many currently used pharmaceutical excipients, which poses a great problem for keeping stability of the active substance in the oral solid dosage form. These problems have been partially solved by an oral dosage form of a tetravalent platinum complex, described in PCT/CZ99/00015 which provides preparation of an oral solid dosage form containing a complex of tetravalent platinum in the form of its soluble inclusion complexes with cyclodextrins, and subsequent lyophilization. However, this method of preparation is complicated and expensive, and the limited capacity of cyclodextrin significantly limits the content of the tetravalent platinum complex present in the cyclodextrin inclusion complex. The possibility of manufacturing a stable oral dosage form containing a complex of tetravalent platinum has been disclosed in patent application CZ 2004-235 which specifies excipients compatible with tetravalent platinum complexes.

The possibility of enterosolvent application of platinum complexes, i.e. their targeted application in the region of small intestine and their possible controlled release in this region, in an oral application has been described in PCT/CZ2004/000017. However, the possibility of oral application of a solid dosage form of platinum complexes, that would allow their colonic release, has not been hitherto described.

Therefore, this invention discloses an oral pharmaceutical composition for a targeted transport of a platinum complex into the colorectal region.

SUMMARY OF THE INVENTION

The above-mentioned objective is achieved by an oral pharmaceutical composition for a targeted transport of a platinum complex into the colorectal region, characterized in that it comprises a mixture of active substance platinum complex of general formula I

wherein
A each independently is an —NH₃ group or an amino group containing 1 to 18 carbon atoms,
B each independently is a halogen atom, a hydroxy group or a —O—C(O)—R group wherein R each independently is hydrogen atom or an alkyl, alkenyl, aryl, aralkyl, alkylamino or alkoxy group containing 1 to 10 carbon atoms or functional derivatives of these groups, and X each independently is a halogen atom or a monocarboxylate group containing 1 to 20 carbon atoms, or X together form a dicarboxylate group containing 2 to 20 carbon atoms, and at least one excipient selected from the group including a saccharide, oligosaccharide, polysaccharide, modified polysaccharide, mucopolysaccharide, protein, oligoprotein, polyprotein, mucoprotein, peptide, oligopeptide and polypeptide, and optionally a lubricant and/or disintegrant, which mixture is optionally compressed into a tablet or contained in a capsule, and this tablet or capsule is optionally coated with a biodegradable layer and/or an outer pH-sensitive colonic layer.

A mixture of the platinum complex of general formula I and at least one excipient selected from the group including a saccharide, oligosaccharide, polysaccharide, modified polysaccharide, mucopolysaccharide, protein, oligoprotein, polyprotein, mucoprotein, peptide, oligopeptide and polypeptide, and optionally a lubricant and/or disintegrant, is advantageously prepared in the form of a granulate, obtained by granulation of the water-wetted mixture of the mentioned platinum complex of general formula I and at least one of the above-mentioned excipients.

The oral pharmaceutical composition is advantageously provided in the form of a tablet, obtained by compression of a mixture of the platinum complex of general formula I and at least one excipient from the group including a saccharide, oligosaccharide, polysaccharide, modified polysaccharide, mucopolysaccharide, protein, oligoprotein, polyprotein, mucoprotein, peptide, oligopeptide and polypeptide, and optionally a lubricant and/or disintegrant, and optionally coated with a biodegradable layer, this tablet being coated with an outer pH-sensitive colonic layer.

The oral pharmaceutical composition is advantageously provided in the form of a capsule containing a mixture of the platinum complex of general formula I and at least one excipient from the group including a saccharide, oligosaccharide, polysaccharide, modified polysaccharide, mucopolysaccharide, protein, oligoprotein, polyprotein, mucoprotein, peptide, oligopeptide and polypeptide, and optionally lubricants and/or disintegrants, this capsule being made of material enabling release of the platinum complex of general formula I only in the large intestine.

The oral pharmaceutical composition is advantageously provided in the form of a capsule containing a mixture of the platinum complex of general formula I and at least one excipient from the group including a saccharide, oligosaccharide, polysaccharide, modified polysaccharide, mucopolysaccharide, protein, oligoprotein, polyprotein, mucoprotein, peptide, oligopeptide and polypeptide, and optionally a lubricant and/or disintegrant, this capsule being coated with a biodegradable layer and/or an outer pH-sensitive colonic layer.

The oral pharmaceutical composition is advantageously provided in the form of a mixture of the platinum complex of general formula I and at least one excipient from the group including a saccharide, oligosaccharide, polysaccharide, modified polysaccharide, mucopolysaccharide, protein, oligoprotein, polyprotein, mucoprotein, peptide, oligopeptide and polypeptide, and optionally a lubricant and/or disintegrant, which mixture is coated with a biodegradable layer and/or an outer pH-sensitive layer.

More advantageously, the oral pharmaceutical composition is advantageously provided in the form of a mixture of the platinum complex of general formula I and at least one excipient from the group including a saccharide, oligosaccharide, polysaccharide, modified polysaccharide, mucopolysaccharide, protein, oligoprotein, polyprotein, mucoprotein, peptide, oligopeptide and polypeptide, and optionally a lubricant and/or disintegrant, which mixture is coated with a biodegradable layer and/or an outer pH-sensitive layer, and is contained in a capsule.

The invention also relates to a method of manufacturing the above-mentioned oral pharmaceutical composition, characterized in that the platinum complex of general formula I is mixed with at least one excipient from the group including a saccharide, oligosaccharide, polysaccharide, modified polysaccharide, mucopolysaccharide, protein, oligoprotein, polyprotein, mucoprotein, peptide, oligopeptide and polypeptide, and optionally with a lubricant and/or disintegrant, whereupon the obtained mixture is optionally wetted with water and granulated to a granulate, and the obtained mixture or the obtained granulate, after optional addition of a lubricant and/or disintegrant, is optionally compacted into tablets or is filled into capsules, and the obtained mixture or the obtained granulate or the obtained tablets or the obtained capsules are optionally coated with a biodegradable layer and/or with an outer pH-sensitive colonic layer.

The granulation of the water-wetted mixture is advantageously carried out in an apparatus in which the surfaces in contact with the mixture to be granulated are inert toward this mixture.

The compacting of the mixture or the granulate into tablets or filling of the mixture or the granulate into capsules is advantageously carried out in an apparatus in which the surfaces in contact with the mixture or with the granulate during their compacting or filling are inert toward this mixture or toward this granulate.

The coating of the mixture or granulate or tablets is advantageously carried out in an apparatus in which the surfaces in contact with the mixture, granulate or tablets to be coated are coated with an inert polymer.

The invention also relates to the above-mentioned oral pharmaceutical composition or this composition prepared by the above-described manner, for use as medicament for treatment of colorectal carcinoma.

The composition of the oral pharmaceutical composition according to the invention guarantees an excellent stability of the tetravalent platinum complex as well as its colonic release, i.e. release only in the colonic region, in oral administration of solid dosage form. According to the literature (Pharma Polymers, Vol. 7, October 2000), during the passage through the digestive tract, in an ideal colonic application 50 to 65% of the active substance is released after 6 hours and 85 to 100% of the active substance is released after 12 hours. This passage lasts for about 2 to 4 hours in the stomach at pH 1 to 5, then for about 3 to 5 hours in the small intestine at pH 5.5 to 7, and finally in the large intestine at pH about 6 to 7.5. To follow continually the release of the active substance, a method has been developed in which the dosage form is tested under paddle-stirring at 50 r.p.m. in a dissolution apparatus USP type II, containing 900 ml 0.1 M HCl, at pH 1.2, the transition to pH 6.8 being achieved by addition of 20.7 g $Na_3PO_4.12H_2O$. The oral pharmaceutical composition according to the invention makes it possible to achieve just the same ideal colonic release of the platinum complex.

The protective excipients, that are present in the pharmaceutical composition according to the invention together with the platinum complex of general formula I and form conjugates with this complex, are as such resistant to enzymatic decomposition in the region of stomach and small intestine, and thus they protect the platinum complex from its premature release in these regions. This concerns polysaccharides, mucopolysaccharides, proteins, oligoproteins, polyproteins, mucoproteins, peptides, oligopeptides and polypeptides. The content of these protective excipients is at least 5% by weight, based on the total weight of the mixture with the platinum complex. Another excipient that may be contained together with the platinum complex in the pharmaceutical composition according to the invention is a modified polysaccharide. This excipient represents only a binder without any effective protective function. In case of its use, the content of this binder is at least 2% by weight, based on the total weight of the mixture with the platinum complex. This binder need not be necessarily present if the binding properties of the above-mentioned protecting excipients in their mixing with water are utilized. On the other hand, if the mentioned mixture contains the platinum complex with only the mentioned binding excipient formed by a modified polysaccharide, the targeted colonic release of the platinum complex has to be ensured by coating the mentioned mixture with a biodegradable layer and/or an outer pH-sensitive colonic layer. The same measures have to be done in case that the pharmaceutical composition contains a saccharide and/or oligosaccharide as a filler and the pharmaceutical composition contains neither of the mentioned protective excipients. Even when the mixture of the platinum complex contains at least one of the above-mentioned protective excipients such as polysaccharides, mucopolysaccharides, proteins, oligoproteins, polyproteins, mucoproteins, peptides, oligopeptides and polypeptides, it is possible to protect the complex from a more intense release by coating the mixture with a biodegradable layer and/or by an outer pH-sensitive colonic layer.

Representative preferred polysaccharides, mucopolysaccharides, proteins, oligoproteins, polyproteins, mucoproteins, peptides, oligopeptides and polypeptides include e.g. amylose, xylan, inulin, dextrin, cyclodextrin, dextrin, dextran esters, chytosan, arabinogalactan, gum guar, glucuronate, pectin, amylopectin, polyaspartam, chondroitin sulfate, hyaluronic acid and collagen. A modified polysaccharide may be e.g. a modified starch.

In order to prevent aggregation of particles of the pharmaceutical composition and to enable its even filling into capsules or compacting into tablets, the oral pharmaceutical composition according to the invention may contain at least one pharmaceutically acceptable lubricant. As a suitable lubricant, magnesium stearate is advantageously used in an amount equal to at least 0.1% by weight, based on the total weight of the pharmaceutical composition mixture. To achieve optimal disintegration of the pharmaceutical composition mixture, and thus also to intensify and accelerate the release of the platinum complex, the oral pharmaceutical composition according to the invention may contain at least one pharmaceutically acceptable disintegrant, advantageously modified polysaccharides. Such disintegrant is advantageously maize and/or wheat and/or rice and/or potato starch, preferably used in an amount of at least 3% by weight, more preferably 3 to 20% by weight, based on the total weight of the pharmaceutical composition mixture.

The biodegradable layer, optionally coating the oral composition mixture as such or optionally coating a tablet into which this mixture is compacted or optionally coating a capsule containing this mixture, consists of polysaccharides or proteins and their derivatives which before entering the large intestine resist the enzymes of the digestive tract but afterwards undergo fission by action of the bacterial microflora present in the large intestine. In the small intestine regions there are colonies of mostly aerobic microflora whereas the large intestine contains an anaerobic bacterial microflora. This specific microflora in the large intestine induces hydrolysis and reduction. Substances, undergoing degradation in this area include e.g. amylose, xylan, inulin, dextrin, cyclodextrin, dextrin, dextran esters, chytosan, arabinogalactan, gum guar, glucuronate, pectin, amylopectin, polyaspartam, chondroitin sulfate, hyaluronic acid and collagen. These substances are often used in combination with synthetic polymers such as e.g. ethyl cellulose, HEC, MPC, MC and HPMC.

The outer pH-sensitive colonic layer, optionally coating the oral composition mixture as such, or coating a tablet into which this mixture is compacted, or coating a capsule containing this mixture, consists of pH-sensitive polymers that form membranes resisting the pH-values in the gastrointestinal tract but dissolve at pH values between 6 and 7. Such polymers are e.g. acrylate or methacrylate polymers and copolymers of the EUDRAGIT S and EUDRAGIT FS type or hydroxypropyl methyl cellulose acetate succinate (HPMCAS) and also their combinations with suitable reagents such as wetting agents and softeners, pigments and lubricants. These polymers, or their combinations, dissolve at pH in the region from 6 to 7, corresponding to the colonic region, and may enable the platinum complex release only after about 3 to 5 hours.

Advantageously, in case of a granulate comprising a mixture of the platinum complex with at least one excipient from the above-mentioned group, this granulate, after mixing with a lubricant and a disintegrant, is filled either into a capsule that afterwards may be coated with an outer pH-sensitive colonic layer, using in this case a gelatin or HPMC capsule, or is filled into a capsule that had been modified in advance for the colonic application. Such modification may particularly consist in that the capsule is made of material, undergoing degradation only by enzymatic action in the colon, such as chytosan, or the capsule body is made of material, resisting the medium of stomach and small intestine but the cap of the capsule is made of material which is dissolved or degraded by action of microflora and at pH 6 to 7 in the colonic region, such material being variously substituted celluloses or acrylate polymers.

Before the final processing into the desired dosage form, the granulate or tablet may also be protected by a layer which either directly protects the platinum complex from the medium of stomach and small intestine or will protect the platinum complex from a pH-sensitive polymer coating that allows specific colonic release of the platinum complex but is not compatible with the platinum complex. In this case there is a synergism between the acidoresistant protection by the pH-sensitive coating and the protection from the digestive enzymes in the stomach or in the small intestine. Such a protective coating may be formed by a layer of at least one substance from a group comprising polysaccharides, mucopolysaccharides, proteins, oligoproteins, polyproteins, mucoproteins, peptides, oligopeptides and polypeptides, examples of which are amylose, inulin, dextrin, cyclodextrin, dextrin, dextran esters, chytosan, arabinogalactan, gum guar, glucuronate, pectin, amylopectin, polyaspartam, chondroitin, hyaluronic acid and collagen, which layer is applied in the form of an aqueous solution or an aqueous-alcoholic hydrogel and which enables protection of the platinum complex during the passage through the stomach and small intestine or protects the platinum complex from direct contact with the subsequently applied pH-sensitive polymer. The weight of dry material of the applied protective coating amounts to at most 50% by weight, based on the total weight of the granulate or tablet. The thus-coated granulate or tablets may be filled into gelatin capsule which already requires no special modification or which may be subsequently coated with another protecting layer. In such case it is possible to use a hard gelatin capsule or advantageously an HPMC capsule.

Particularly effective protection, and thus targeted colonic application, of the platinum complex can be achieved when a granulate, coated with a layer protecting from enzymatic degradation in stomach or small intestine, or an uncoated granulate filled into hard gelatin or HPMC capsules, is coated with an outer pH-sensitive layer that dissolves only at pH 6 to 7.5, i.e. in the colonic region. Preferred pharmaceutically acceptable substances enabling such coating are hydroxypropyl methyl cellulose acetate succinate (HPMCAS), methacrylic acid and its derivatives, preferably its polymers and copolymers, such as EUDRAGIT S and EUDRAGIT FS, either e.g. in the form of their plastified aqueous dispersions EUDRAGIT S 30D or EUDRAGIT FS 30D or e.g. in the form of organic or aqueous-alcoholic solutions EUDRAGIT S 12.5, optionally their mixtures in desired ratios, the weight of the coat dry matter being less than or equal to 15% by weight, preferably 4 to 10% by weight, based on the total weight of the granulate.

Alternatively, the capsule body may also be coated by material of the protecting layer that protects from digestive enzymes in the stomach or the small intestine, used in a mixture with other polymers.

Polymer, facilitating the coating and assisting the given antienzymatic protection, may be EC and/or MC and/or HEC and/or HPC and/or HPMC, or their mixture in a desired ratio. These mixtures are applied as aqueous or aqueous-alcoholic dispersions, the weight of the coat dry matter being less than or equal to 30% by weight, preferably 10 to 15% by weight, based on the total weight of the coat.

Before coating with a biodegradable layer and/or an outer pH-sensitive layer, the dosage forms in the form of the mixture, particularly granulate, or in the form of tablets, may be coated with an inert isolating layer that should protect the dosage form from the biodegradable layer or from the outer pH-sensitive colonic layer in case that no biodegradable layer has been applied. This isolating layer may be e.g. formed by spraying 15% by weight, based on the total weight of the dosage form, of hydrogel prepared by dissolution of dextran, with optional addition of glycerol as plastifier. Alternatively, 10% by weight of collagen or 5% by weight of guar gum hydrogel may be used, with optional addition of glycerol as plastifier.

In the preparation of wet granulate, representing one of the forms of the oral pharmaceutical composition according to the present invention, it has been surprisingly found that the wet granulate undergoes undesired chemical reactions on contact with metallic surface of conventional pharmaceutical technological equipment for processing and manufacturing solid dosage forms. This fact hinders the use of standard manufacturing techniques such as compacting in the preparation of the granulate or compressing into tablets without surface modification of the metallic parts in question. Therefore, the wet granulate, representing one of the forms of the oral pharmaceutical composition according to this invention, should be advantageously processed in an equipment whose surfaces coming into contact with the granulated mixture are inert towards the mixture. Good inert materials proved to be e.g. glass, porcelain, teflon or enamel.

During the coating of drug forms according to the invention, the mentioned inert isolating layer may be damaged and thus the platinum complex might come into contact with metallic parts of the coating apparatus. This may occur particularly when the coating is carried out in a current coating equipment with metallic surfaces, such as e.g. drum coating machines, top spray fluid bed dryers, Wusters or rotoprocessors. However, this situation can surprisingly be avoided by coating the equipment surfaces in contact with the dosage form with a film of an inert material which at the same time forms the inert isolating layer.

The oral pharmaceutical composition according to the invention enables one-dose application of 5 to 500 mg, preferably 50 to 350 mg, of the platinum complex of general formula I. The oral pharmaceutical composition according to the invention is stable, can be easily prepared and its composition is simple.

In the following part the invention will be explained in more detail using individual examples of its execution which however are only illustrative and do not limit its scope. Within the framework of these examples, the employed platinum complex of general formula I is af-bis(acetato)-b-(1-adamantylamine)-c-ammine-de-dichloroplatinum(IV) complex of formula II

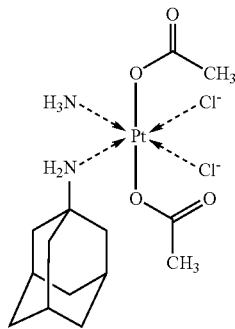

(II)

This complex of summary formula $C_{14}H_{26}Cl_2N_2O_4Pt$ and of molecular weight 552.35 contains (acetato)-(1-adamantylamine)-ammine-trichloroplatinum(IV) complex of structural formula $Pt(ac)(am)(NH_3)Cl_3$. as principal detectable impurity. The mentioned specific platinum(IV) complex of formula II, together with its antitumor effects, is described in the patent document PCT/CZ99/00015 where it is denoted as LA 12. It is sparingly soluble in water, its solubility being 0.03 g/100 ml, has a low bulk density amounting to 0.21 g/ml and a low tap density amounting to 0.42 g/ml, and an extremely high electrostatic charge.

EXAMPLES

Example 1

Composition and Method of Manufacturing Granulate of Pharmaceutical Composition Containing Platinum Complex of Formula II The weights specified in the examples are given in parts by weight.

| | |
|---|---|
| 1. Platinum complex of formula II | 200.00 |
| 2. Modified maize starch | 20.00 |
| 3. Lactose | 200.00 |
| 4. Modified maize starch | 42.00 |
| 5. Magnesium stearate | 4.20 |

Preparation Procedure
  Components 1-3 are mixed in a high-speed mixer.
  Water (70-90 parts by weight) is added.
  The mixture is mixed in a high-speed mixer.
  The granulate is dried at 70° C. to humidity of 2-4%.
  The dry granulate is ground e.g. in a porcelain ball mill to obtain material of desired particle size.
  Components 4 and 5 are added and the mixture is mixed in a cube mixer for 15 minutes.

Example 2

Method of Filling the Granulate of Pharmaceutical Composition Containing Platinum Complex of Formula II, Prepared According to Example 1

The granulate, obtained according to Example 1, is filled into hard gelatin, colonic, chytosan or HPMC capsules of size ranging from 5 to 000, corresponding to the range of granulate weight from 116.55 mg to 815.85 mg, which enables dosage from 50 mg to 350 mg of the active component, or it is compacted into tablets, corresponding to analogous weights.

Example 3

Composition and Method of Manufacturing Granulate of Pharmaceutical Composition Containing Platinum Complex of Formula II The weights specified in the examples are given in parts by weight.

| | |
|---|---:|
| 1. Platinum complex of formula II | 200.00 |
| 2. Modified maize starch | 62.00 |
| 3. Dextran | 200.00 |
| 4. Magnesium stearate | 4.20 |

Preparation Procedure
  Components 1-3 are mixed in a high-speed mixer.
  Water (80-160 parts by weight) is added.
  The mixture is mixed in a high-speed mixer.
  The granulate is dried at 70° C. to humidity of 2-4%.
  The dry granulate is ground e.g. in a porcelain ball mill to obtain material of desired particle size.
  Component 4 is added and the mixture is mixed in a cube mixer for 15 minutes.

Example 4

Method of Filling the Granulate of Pharmaceutical Composition Containing Platinum Complex of Formula II, Prepared According to Example 3

The granulate, obtained according to Example 3, is filled into hard gelatin, colonic, chytosan or HPMC capsules of size ranging from 5 to 000, corresponding to the range of granulate weight from 116.55 mg to 815.85 mg, which enables dosage from 50 mg to 350 mg of the active component, or it is compacted into tablets, corresponding to analogous weights.

Example 5

Composition and Method of Manufacturing Granulate of Pharmaceutical Composition Containing Platinum Complex of Formula II The weights specified in the examples are given in parts by weight.

| | |
|---|---:|
| 1. Platinum complex of formula II | 200.00 |
| 2. Modified maize starch | 62.00 |
| 3. Dextran | 200.00 |

Preparation Procedure
  Components 1-3 are mixed in a high-speed mixer.
  Water (80-160 parts by weight) is added.
  The mixture is mixed in a high-speed mixer.
  The granulate is dried at 70° C. to humidity of 2-4%.
  The dry granulate is ground e.g. in a porcelain ball mill to obtain material of desired particle size.

Example 6

Method of Fluidized Bed Application of Isolating Layer onto Granulate of Pharmaceutical Composition Containing Platinum Complex of Formula II, Prepared According to Example 5

| | |
|---|---|
| Equipment: | Wurster |
| Charge of granulate: | 0.50 kg |
| Inlet air temperature: | 50-70° C. |
| Outlet air temperature: | 30-50° C. |
| Spray rate: | 6-25 g/min |
| Nozzle diameter: | 0.8 mm |
| Coating layer weight: | 4-30% by weight |

The spraying is executed until achieving the target weight gain of the granulate corresponding to the desired weight of the coating layer.

The spraying is carried out using 1% (by weight) hydrogel prepared by dissolution of dextran, with possible addition of glycerol as plasticizer. Alternatively, 10% (by weight) collagen or 5% (by weight) hydrogel of quar gum may be used, with possible addition of glycerol as plasticizer.

The coating also may be carried out in a conventional drum coating apparatus.

Example 7

Method of Fluidized Bed Application of Isolating Layer onto Tablets of Pharmaceutical Composition Containing Platinum Complex of Formula II, Prepared According to Examples 2 and 4

| | |
|---|---|
| Equipment: | Wurster |
| Charge of cores: | 0.50 kg |
| Inlet air temperature: | 50-70° C. |
| Outlet air temperature: | 40-60° C. |
| Spray rate: | 6-18 g/min |
| Nozzle diameter: | 0.8 mm |
| Coating layer weight: | 5-30% by weight |

The spraying is executed until achieving the target weight gain of the dosage form, corresponding to the desired weight of the coating layer.

The spraying is carried out using 15% (by weight) hydrogel prepared by dissolution of dextran, with possible addition of glycerol as plasticizer. Alternatively, 10% (by weight) collagen or 5% (by weight) hydrogel of quar gum may be used, with possible addition of glycerol as plasticizer.

The coating also may be carried out in a conventional drum coating apparatus.

Example 8

Method of Fluidized Bed Application of pH-Sensitive Layer onto Granulate of Pharmaceutical Composition Containing Platinum Complex of Formula II, Prepared According to Example 6

| Equipment: | Wurster |
|---|---|
| Charge of granulate: | 0.50 kg |
| Inlet air temperature: | 50-70° C. |
| Outlet air temperature: | 24-50° C. |
| Spray rate: | 6-25 g/min |
| Nozzle diameter: | 0.8 mm |
| Coating layer weight: | 8-12% by weight or 6-10 mg/cm² of coat dry matter |

The spraying is executed until achieving the target weight gain of the granulate, corresponding to the desired weight of the coating layer.

The spraying is carried out using 20% (by weight) aqueous dispersion of Eudragit S or FS, or 10% (by weight) aqueous dispersion of HPMCAS. The coating also may be carried out in a conventional drum coating apparatus.

Example 9

Method of Fluidized Bed Application of Ph-Sensitive Layer onto Capsules Containing Platinum Complex of Formula II, Prepared According to Examples 2 and 4, and onto Tablets Containing Platinum Complex of Formula II, Prepared According to Example 7

| Equipment: | Wurster |
|---|---|
| Charge of cores: | 0.50 kg |
| Inlet air temperature: | 50-70° C. |
| Outlet air temperature: | 25-60° C. |
| Spray rate: | 6-18 g/min |
| Nozzle diameter: | 0.8 mm |
| Coating layer weight: | 8-12% by weight or 6-10 mg/cm² of coat dry matter |

The spraying is executed until achieving the target weight gain of the granulate, corresponding to the desired weight of the coating layer.

The spraying is carried out using 20% (by weight) aqueous dispersion of Eudragit S or FS, or 10% (by weight) aqueous dispersion of HPMCAS. The coating also may be carried out in a conventional drum coating apparatus.

Example 10

Method of Fluidized Bed Application of an Enzymatically Degradable Layer onto Gelatin and HPMC Capsules Containing Platinum Complex of Formula II, Prepared According to Examples 2 and 4

| Equipment: | Wurster |
|---|---|
| Charge of granulate: | 0.50 kg |
| Inlet air temperature: | 50-70° C. |
| Outlet air temperature: | 24-50° C. |
| Spray rate: | 6-25 g/min |
| Nozzle diameter: | 0.8 mm |
| Coating layer weight: | 10-30% by weight |

The spraying is executed until achieving the target weight gain of the granulate corresponding to the desired weight of the coating layer.

The spraying is carried out using 5% (by weight) aqueous dispersion of ethyl cellulose (Surrelease, or Aquacoat) with 10% (by weight) aqueous dispersion of amylose. The coating also may be carried out in a conventional drum coating apparatus.

Example 11

Dissolution Test of the Final Dosage Form by Paddle Method

| Speed: | 50 rpm |
|---|---|
| Temperature: | 37 + 0.5° C. |
| Volume: | 900 ml |

The test is performed for 2 hours in 0.1 M HCl, pH 1.2, then pH is adjusted to 6.8 by addition of about 20.7 g $Na_3PO_4 \cdot 12 H_2O$ and the test is continued for further 8 hours. During 2 hours the dosage form must not release more than 5% of the active substance, after 6 hours more than 60% of the active substance, and at least 85% of the active substance must be released after total 12 hours.

The invention claimed is:

1. An oral pharmaceutical composition for targeted transport of a platinum complex into the colorectal region, comprising:
   a mixture of platinum complex of general formula (II)

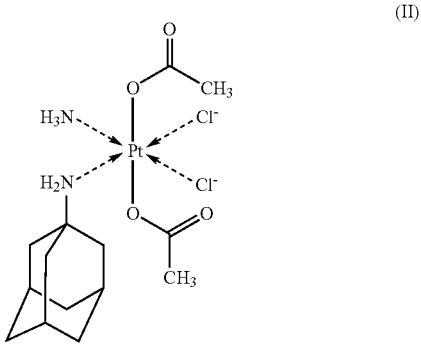

(II)

and at least one excipient selected from the group consisting of: a saccharide, oligosaccharide, polysaccharide, modified polysaccharide, mucopolysaccharide, protein, oligoprotein, polyprotein, mucoprotein, peptide, oligopeptide and polypeptide, as well as one of a lubricant and/or disintegrant.

2. The oral pharmaceutical composition according to claim 1, wherein the mixture of the platinum complex of general formula (II) and at least one excipient selected from the group consisting of: a saccharide, oligosaccharide, polysaccharide, modified polysaccharide, mucopolysaccharido, protein, oligoprotein, polyprotein, mucoprotein, peptide, oligopeptide and polypeptide, and one of a lubricant and/or disintegrant, is in the form of a granulate, obtained by granulation of a water-wetted mixture of the mentioned platinum complex of general formula I and at least one of the above-mentioned excipients.

3. An oral pharmaceutical composition according to claim 1, wherein it is in the form of a tablet obtained by compacting a mixture of the platinum complex of general formula (II) and at least one excipient selected from the group consisting of: a saccharide, oligosaccharide, polysaccharide, modified polysaccharide, mucopolysaccharide, protein, oligoprotein, polyprotein, mucoprotein, peptide, oligopeptide and polypeptide, and optionally one of a lubricant and/or disintegrant, and coated with a biodegradable layer, wherein said tablet is coated with an outer pH-sensitive colonic layer.

4. An oral pharmaceutical composition according to claim 1, wherein it is in the form of a capsule containing a mixture of the platinum complex of general formula (II) and at least one excipient selected from the group consisting of: a saccharide, oligosaccharide, polysaccharide, modified polysaccharide, mucopolysaccharide, protein, oligoprotein, polyprotein, mucoprotein, peptide, oligopeptide and polypeptide, and one of a lubricant and/or disintegrant, wherein said capsule consists of material enabling release of the platinum complex of general formula I only in the large intestine.

5. An oral pharmaceutical composition according to claim 1, wherein it is in the form of a capsule containing a mixture of the platinum complex of general formula (II) and at least one excipient selected from the group consisting of: a saccharide, oligosaccharide, polysaccharide, modified polysaccharide, mucopolysaccharide, protein, oligoprotein, polyprotein, mucoprotein, peptide, oligopeptide and polypeptide, and one of a lubricant and/or a disintegrant, wherein said capsule is coated with one of a biodegradable layer and/or an outer pH-sensitive colonic layer.

6. An oral pharmaceutical composition according to claim 1, wherein it is in the form of a mixture of the platinum complex of general formula (II) and at least one excipient selected from the group consisting of: a saccharide, oligosaccharide, polysaccharide, modified polysaccharide, mucopolysaccharide, protein, oligoprotein, polyprotein, mucoprotein, peptide, oligopeptide and polypeptide, and one of a lubricant and/or disintegrant, wherein said mixture is coated with one of a biodegradable layer and/or an outer pH-sensitive layer.

7. An oral pharmaceutical composition according to claim 6, wherein it is in the form of a mixture of the platinum complex of general formula (II) on and at least one excipient selected from the group consisting of: a saccharide, oligosaccharide, polysaccharide, modified polysaccharide, mucopolysaccharide, protein, oligoprotein, polyprotein, mucoprotein, peptide, oligopeptide and polypeptide, and one of a lubricant and/or disintegrant, wherein said mixture is coated with one of a biodegradable layer and/or an outer pH-sensitive layer and contained in a capsule.

8. A method for producing an oral pharmaceutical composition for targeted transport of a platinum complex into the colorectal region comprising the steps of:
providing a platinum complex of general formula (II);

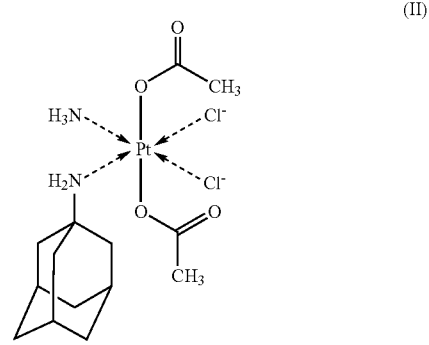

mixing the platinum complex of general formula (II) with at least one excipient selected from the group consisting of: a saccharide, oligosaccharide, polysaccharide, modified polysaccharide, mucopolysaccharide, protein, oligoprotein, polyprotein, mucoprotein, peptide, oligopeptide and polypeptide, and with one of a lubricant and/or disintegrant, whereupon the mixture obtained is wetted with water and granulated under formation of granulate, and the obtained mixture or the obtained granulate, after addition of one of a lubricant and/or disintegrant, is one of compacted into tablets and filled into capsules, and the mixture obtained or the granulate obtained or the tablets obtained or the capsules obtained are coated with one of a biodegradable layer and/or an outer pH-sensitive colonic layer.

9. The method according to claim 8, wherein the granulation of the water-wetted mixture is performed in an apparatus in which surfaces in contact with the mixture being granulated are inert toward this mixture.

10. A method according to claim 8, wherein the compacting into tablets or filling into capsules of the mixture or of the granulate is carried out in an apparatus in which surfaces in contact with the compacted or filled mixture or with the compacted of filled granulate are inert toward this mixture or this granulate.

11. A method according to claim 8, wherein the coating of the mixture or granulate or tablets is performed in an apparatus in which surfaces in contact with the mixture being coated or with the granulate being coated or with the tablets being coated are coated with an inert polymer.

12. An oral pharmaceutical composition according to claim 1, wherein the excipient is saccharide.

13. An oral pharmaceutical composition for targeted transport of a platinum complex into the colorectal region, comprising:
a mixture of platinum complex of general formula (II)

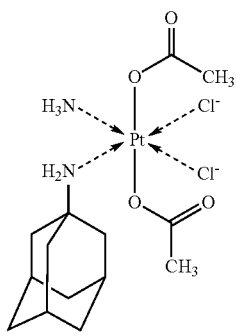

(II)

and at least one excipient selected from the group consisting of: protein and peptide; and
wherein said mixture is one of: compressed into a tablet; contained in a capsule; and compressed into a tablet that is coated with one of a biodegradable layer and an outer pH-sensitive colonic layer.

14. An oral pharmaceutical composition for targeted transport of a platinum complex into the colorectal region, comprising:
a mixture of platinum complex of general formula (II)

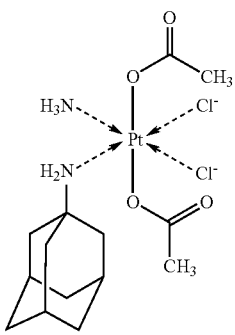

(II)

and at least one excipient selected from the group consisting of: protein and peptide.

15. An oral pharmaceutical composition for targeted transport of a platinum complex into the colorectal region as claimed in claim 1, wherein said mixture is one of: compressed into a tablet; contained in a capsule; and compressed into a tablet that is coated with one of a biodegradable layer and an outer pH-sensitive colonic layer.

* * * * *